United States Patent [19]
Fuller et al.

[11] Patent Number: 5,115,669
[45] Date of Patent: May 26, 1992

[54] MEASURING SHEAR VISCOSITY OF FLUIDS

[75] Inventors: Gerald G. Fuller, Palo Alto, Calif.; Ronald F. Garritano, Flemington; Paul Mode, Westfield, both of N.J.

[73] Assignee: Rheometrics, Inc., Piscataway, N.J.

[21] Appl. No.: 593,231

[22] Filed: Oct. 5, 1990

[51] Int. Cl.[5] ............................................. G01N 11/00
[52] U.S. Cl. ..................................................... 73/54.39
[58] Field of Search ................................. 73/60, 59, 54

[56] References Cited

U.S. PATENT DOCUMENTS 4,077,251  3/1978  Winter ...................................... 73/59
4,570,478  2/1986  Soong ....................................... 73/60

*Primary Examiner*—Hezron E. Williams
*Assistant Examiner*—Shu-Cheng Kau
*Attorney, Agent, or Firm*—Samuelson & Jacob

[57] ABSTRACT

Apparatus and method for measuring the shear viscosity of a fluid urges sample fluid through a gap between a sleeve having an axial passage and a pin extending axially into the passage in the sleeve to subject the sample fluid to shear while measuring the axial force tending to move the pin and the sleeve axially away from one another, the axial force being indicative of the shear viscosity of the sample fluid.

21 Claims, 2 Drawing Sheets

MEASURING SHEAR VISCOSITY OF FLUIDS

The present invention relates generally to the measurement of the viscosity of fluids and pertains, more specifically, to the measurement of shear viscosity, especially in relatively low-viscosity fluids.

Investigations into the measurement of extensional viscosity in fluids, and especially in low-viscosity fluids such as paints, inks, coatings and certain oils, have led to the development of a rheometer of relatively simple design. Thus, in an article entitled *Extensional Viscosity Measurements for Low-Viscosity Fluids,* published in the Journal of Rheology, 31(3), 235–249 (1987), there is suggested a rheometer in which the fluid is either sucked into or blown out of opposed nozzles and measurement of the force required to maintain the nozzles at a fixed distance apart as a function of flow rate yields a determination of extensional viscosity. It would be advantageous to have available the ability to measure the shear viscosity of these same and similar fluids in a similarly simple manner utilizing a rheometer of relatively simple construction.

The present invention provides a rheometer and a method for the measurement of the shear viscosity of fluids, and especially low-viscosity fluids such as paints, inks, coatings and some oils, utilizing a simplified arrangement of component parts and a simple procedure, and accomplishes several objects and advantages, some of which are summarized as follows: Accomplishes the measurement of shear viscosity with increased sensitivity, thereby enabling accurate measurements, even in fluids of relatively low viscosity; enables an increased dynamic range for measuring a wider range of viscosities with increased accuracy; requires only a relatively short residence time of the sample fluid in the instrument for measurement of viscosity of the fluid, thereby reducing any tendency toward increasing the temperature of the fluid as the measurement is made; enables the measurement of both extensional viscosity and shear viscosity in the same basic apparatus, utilizing a relatively simple modification of a single instrument, thereby providing a greater amount of highly useful data at minimal additional expense; accomplishes ease of operation for accurate and reliable results with reduced complexity; and provides an instrument of relatively simple construction and reliable operation for service over a relatively long life.

The above objects and advantages, as well as further objects and advantages are attained by the present invention, which may be described as measuring the shear viscosity of a sample fluid having given flow characteristics by establishing an axially extending gap of predetermined radial and axial dimensions between a first member and a second member, the gap including an entrance and an exit, moving the sample fluid through the gap and establishing a pressure in the sample fluid at the entrance of the gap greater than the pressure in the sample fluid at the exit of the gap so as to urge the sample fluid through the gap, from the entrance to the exit, at a known volumetric flow rate, the predetermined radial and axial dimensions of the gap being related to the flow characteristics of the sample fluid such that the sample fluid is subjected to shear as the sample fluid passes through the gap, applying the pressure at the entrance of the gap to one of the first and second members to establish an axial force tending to move that one of the first and second members in the direction axially away from the other of the first and second members as the sample fluid passes through the gap, and measuring the total force tending to move the first and second members in the direction axially away from one another, as the sample fluid passes through the gap, which total force is indicative of the shear viscosity of the sample fluid.

The invention will be understood more fully, while still further objects and advantages will become apparent, in the following detailed description of a preferred embodiment of the invention illustrated in the accompanying drawing, in which.

Figure 1:
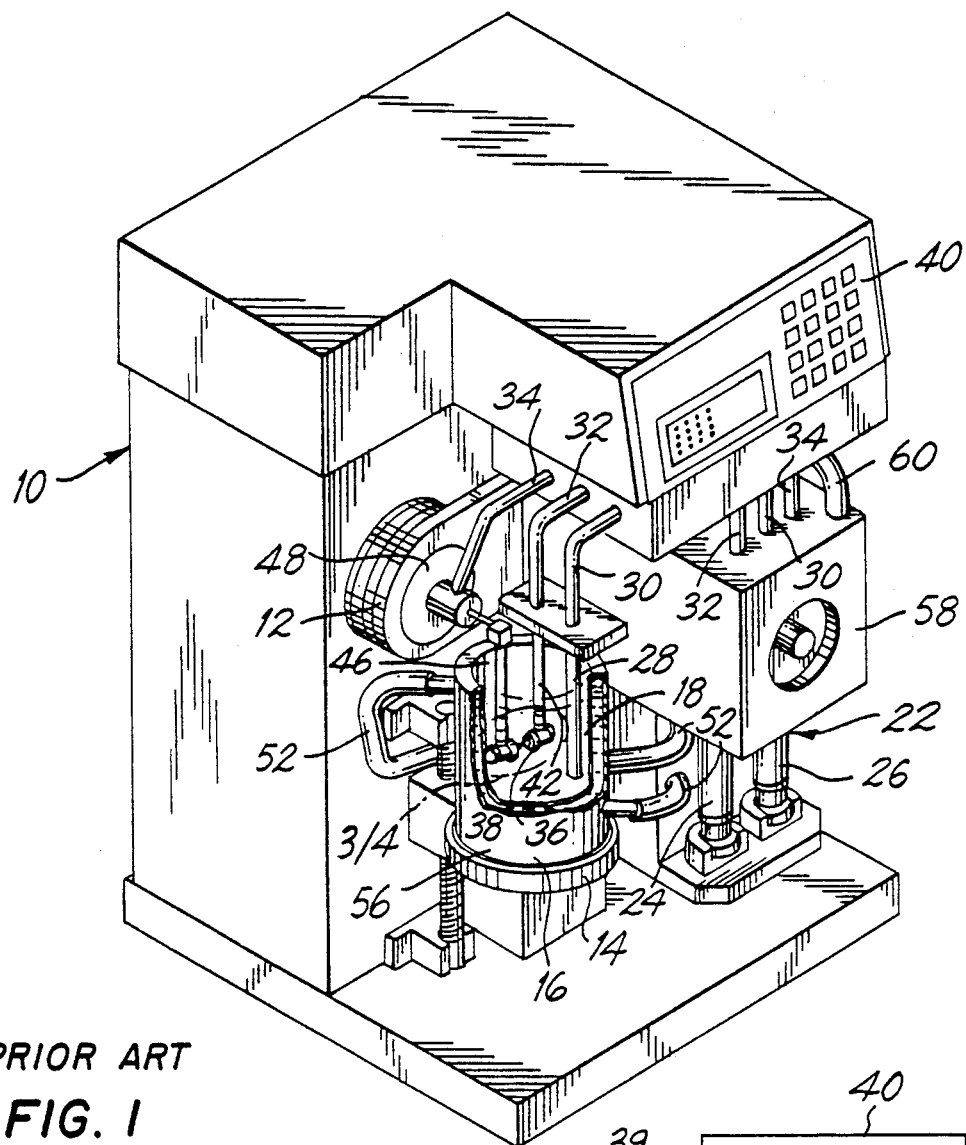
FIG. 1 is a pictorial perspective view of an extensional viscosity rheometer illustrative of the prior art.
Figure 2:
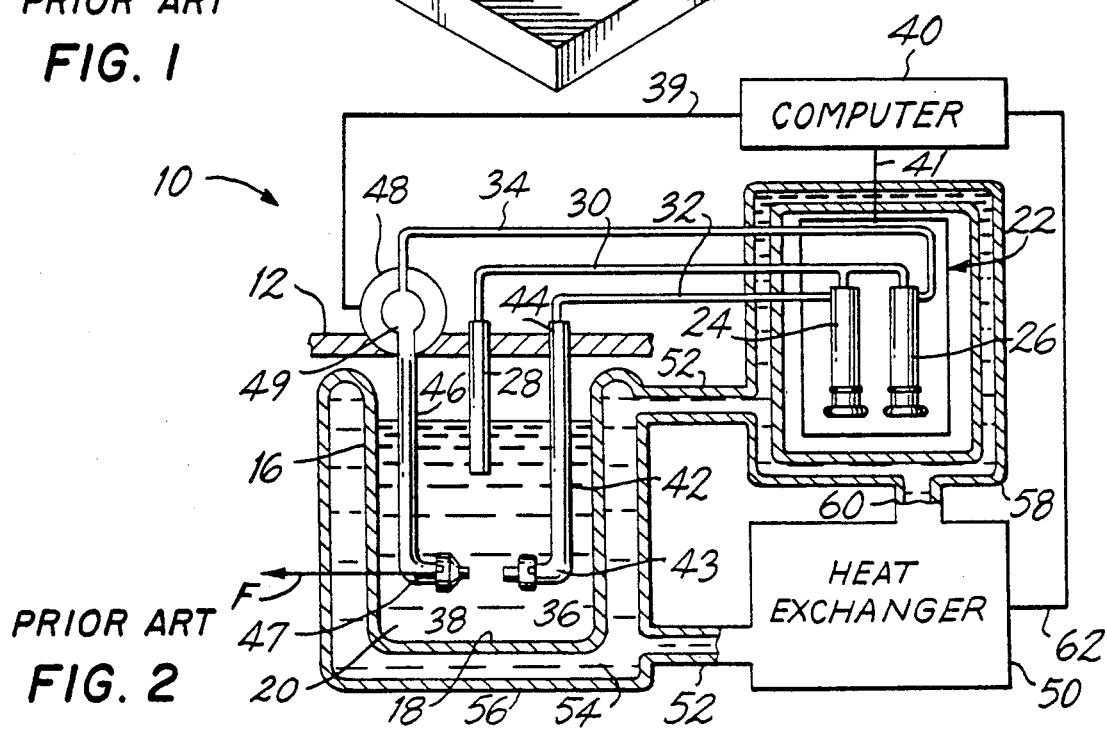
FIG. 2 is a schematic diagram of the instrument of FIG. 1.
Figure 3:
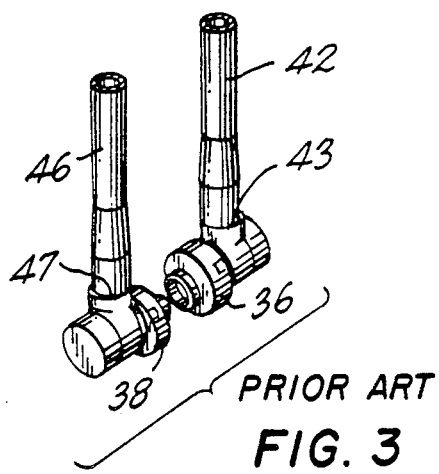
FIG. 3 is an enlarged pictorial perspective view of a portion of the instrument indicated at 3 in FIG. 1.

Referring now to the drawing, and especially to FIGS. 1 through 3 thereof, an extensional viscosity rheometer is illustrated generally at 10 and is seen to include a frame 12 having a platform 14 upon which rests a cup 16 for containing a reservoir 18 of a sample fluid 20. A pump assembly 22 utilizes a pair of syringe pumps 24 and 26 which draw sample fluid 20 from the reservoir 18, through an inlet tube 28 which extends into the sample fluid 20 in the reservoir 18 and communicates with the pump assembly 22 through an inlet conduit 30, to circulate fluid 20 through respective outlet conduits 32 and 34 to opposed nozzles 36 and 38 immersed in the sample fluid 20 in reservoir 18. A computer 40 controls the pump assembly 22, through line 41, so as to provide a selected known volumetric flow of fluid 20 through the circuit which includes the inlet tube 28, the inlet conduit 30, the pumps 24 and 26, the outlet conduits 32 and 34, and the nozzles 36 and 38. By blowing the fluid 20 out of the opposed nozzles 36 and 38, uniaxial compressive flows are approximated and tensile stresses are developed which induce a force F which, in turn, tends to move the nozzles 36 and 38 away from one another. Nozzle 36 is carried by an arm 42, at the far end 43 of the arm 42, and is fixed against movement in response to that force by virtue of the affixation of arm 42 to frame 12 at the near end 44 of the arm 42. Nozzle 38 is carried by another arm 46, at the far end 47 of the arm 46, and the arm 46 is coupled, at the near end 49 of the arm 46, to a force-measuring means illustrated in the preferred form as a force-rebalancing transducer 48 mounted on the frame 12. Force-rebalancing transducer 48 measures the force F tending to move nozzle 38 away from nozzle 36 and transmits information pertaining to that force F, via line 39, to computer 40, without movement of nozzle 38 relative to nozzle 36. The nature and operation of force-rebalancing transducer 48 is described in U.S. Pat. No. 4,601,195 wherein there is disclosed a rheometer which employs a similar force-rebalancing transducer. The dimensions of the orifices of nozzles 36 and 38 are known, as is the volumetric flow rate of the sample fluid 20 through the nozzles 36 and 38. The lever arm provided by the length of the arm 46, between the far end 47 and the near end 49 thereof, increases the sensitivity of the measurement of force F by the force-rebalancing transducer 48. The force F measured by the force-rebalancing transducer 48 thus is indicative of the extensional viscosity of the sample fluid 20 and computer 40 computes the extensional viscosity of sample fluid 20, based upon the measured force F, all as described in greater detail in the above cited article, *Extensional Viscosity Measurements for Low-Viscosity Fluids*.

Since the measured viscosity is related to the temperature of the sample fluid 20, the instrument 10 is provided with heat exchange means for maintaining the sample fluid at essentially constant temperature. Thus, a heat exchanger 50 and connecting conduits 52 circulate a heat exchange medium 54 to a jacket 56 integral with the cup 16 to maintain the sample fluid 20 in the reservoir 18 at a constant temperature. Likewise, the pump assembly 22 is encased within a jacket 58 connected to heat exchanger 50 by conduits 52 and 60 for maintaining the desired constant temperature in the sample fluid 20. Heat exchanger 50 is itself under the control of computer 40, through line 62.

Figure 4:
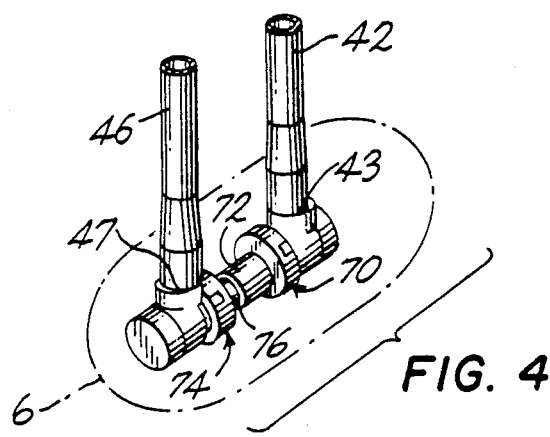
FIG. 4 is an enlarged pictorial perspective view of a portion of the instrument indicated at 4 in FIG. 1, modified for operation in accordance with the present invention.
Figure 5:
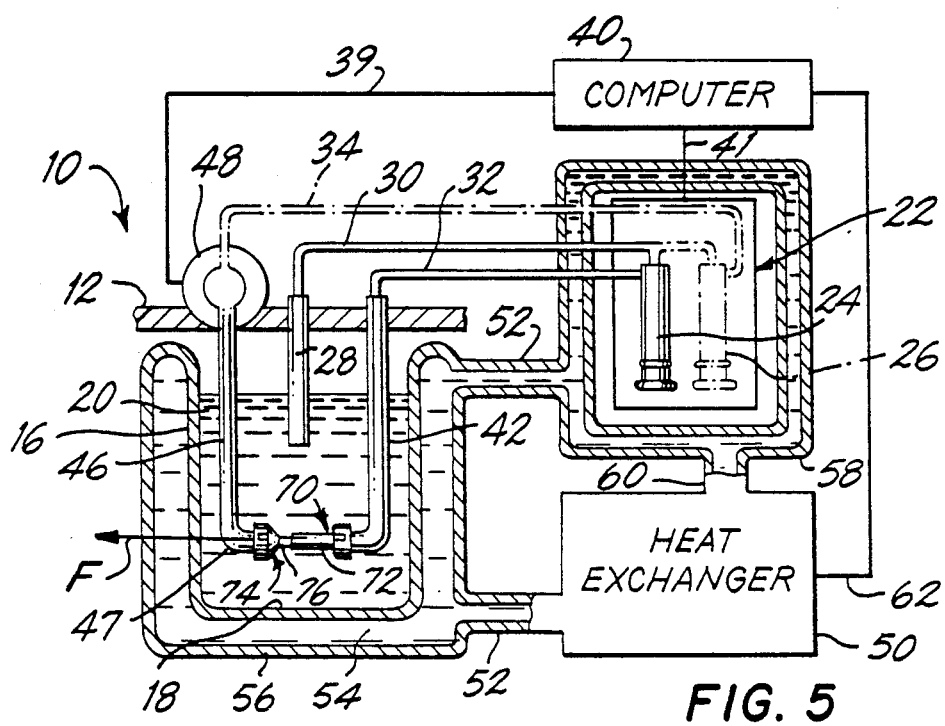
FIG. 5 is a schematic diagram of the instrument, modified for operation in accordance with the present invention.

Turning now to FIGS. 4 and 5, instrument 10 is adapted readily to the measurement of shear viscosity so that a simple and economical apparatus and procedure becomes available for determining the shear viscosity of a sample fluid being tested in instrument 10 for extensional viscosity. Thus, the nozzles 36 and 38 have been replaced, respectively, by a first member 70 which includes a sleeve 72, and a second member 74 which includes a pin 76. The syringe pump 26 has been disabled, so that sample fluid 20 is drawn from reservoir 18 in cup 16 and is circulated by pump assembly 22 only to the sleeve 72. In the alternative, nozzle 36 can be replaced by second member 74 and nozzle 38 can be replaced by first member 70, in which case syringe pump 24 would be disabled and syringe pump 26 would circulate sample fluid 20 to sleeve 72.

Figure 6:
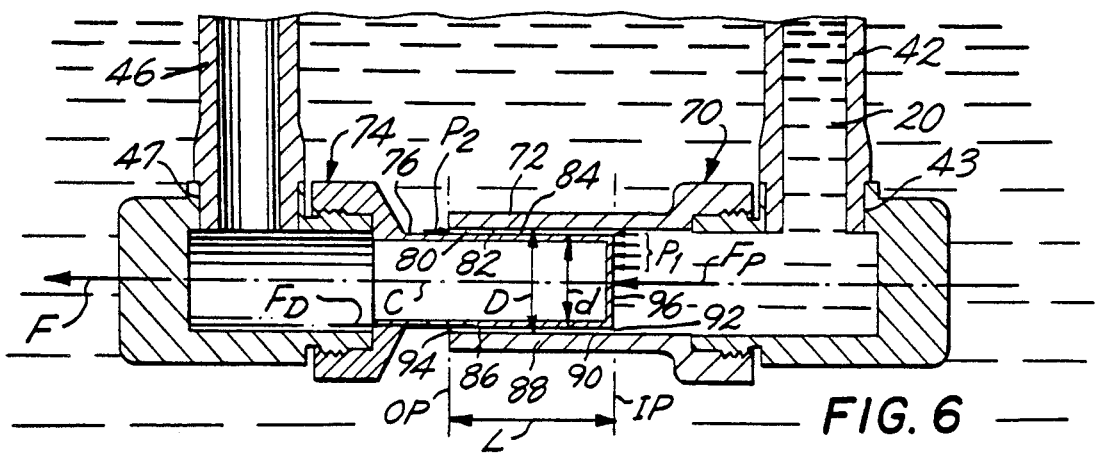
FIG. 6 is an enlarged longitudinal cross-sectional view of the portion of instrument indicated at 6 in FIG. 4.

As best seen in FIG. 6, sleeve 72 has a passage 80 which includes a cylindrical inner surface 82 extending axially along the sleeve 72, the inner surface 82 having a central axis C and a constant diameter D along the length of the inner surface 82. Pin 76 has a cylindrical configuration extending along the same central axis C and including an outer surface 84 with a constant diameter d along the length of the outer surface 84. An end portion 86 of the pin 76 extends into a corresponding portion 88 of the sleeve 72 to establish an annular gap 90 of predetermined axial and radial dimensions in the space between the inner surface 82 of the passage 80 and the outer surface 84 of the pin 76. The axial and radial dimensions of gap 90 are determined by the difference between the larger diameter D of the inner surface 82 of the passage 80 and the smaller diameter d of the outer surface 84 of the pin 76, and by the length L of the end portion 86 of the pin 76 and the corresponding portion 88 of the sleeve 72. In the preferred embodiment, the gap 90 has an annular cross-sectional configuration and the central axis C is oriented horizontally so that the gap 90 extends axially in a horizontal direction.

As set forth above, the far ends 43 and 47 of the respective arms 42 and 46 are immersed in the sample fluid 20 in the reservoir 18; thus, the gap 90, which includes an entrance 92, located at radial plane IP, and an exit 94, located at radial plane OP, and the corresponding portions 86 and 88 of the pin 76 and the sleeve 72 all are immersed in the sample fluid 20 in reservoir 18. The pump assembly 22, under the control of computer 40, serves as a metering means for moving the sample fluid 20 at a selected known volumetric flow rate through the instrument 10 along the circuit extending out of the reservoir 18 and back into the reservoir 18, which circuit includes the inlet tube 28, the inlet conduit 30, the syringe pump 24, the conduit 32, and the gap 90 between the sleeve 72 and the pin 76, so that the sample fluid 20 passes through the gap 90 at the selected known volumetric flow rate. The axial dimension (L) and the radial dimension $[\frac{1}{2}(D-d)]$ of the gap 90 are chosen taking into account the known characteristics of the sample fluid 20 so that the fluid 20 passing through the gap 90 is subjected to shear as the fluid 20 passes through the gap 90. Thus, the sleeve 72 and the pin 76 may be selected from sleeves and pins supplied in a variety of different dimensions to accommodate a variety of sample fluids.

The transducer 48 measures the force F exerted on the pin 76 as the sample fluid 20 passes through the gap 90. Since there is no relative movement between the pin 76 and the sleeve 72, the force F is measured with great accuracy. Force F is comprised of two components: The first component of force F is the frictional force or drag $F_d$ acting upon the portion 86 of the outer surface 84 of the pin 76 as the fluid 20 passes through the gap 90. The second component of force F is the force $F_p$ exerted by the pressure $P_1$ of the fluid 20 at the radial plane IP, adjacent entrance 92 of gap 90, acting upon the flat end face 96 of the pin 76, which end face 96 provides a portion of known radial area established by the diameter d of the outer surface 84. The pressure $P_1$ of the fluid 20 in passage 80, adjacent entrance 92 of gap 90, at the end face 96 of the pin 76 is a result of the pressure difference between the Pressure $P_1$ at the entrance 92 of the gap 90 and the pressure $P_2$ at the exit 94 of the gap 90 generated by the resistance in gap 90 to the flow of the sample fluid 20 through the gap 90 and is a function of the shear viscosity of the fluid 20. Since the pressure $P_1$ acts upon a relatively large known radial area of the pin 76, the force $F_p$ is large and the sensitivity of the instrument 10 is increased. The availability of a large force $F_p$ increases the dynamic range of the instrument 10 so that low shear viscosities may be measured with increased accuracy. The shear viscosity is then calculated, by the computer 40, from the measured force F, utilizing the known parameters, namely, the volumetric flow rate of the sample fluid 20 through the gap 90, the axial and radial dimensions of the gap 90, and the radial area of the pin 76 acted upon by pressure $P_1$. While in the illustrated preferred embodiment of the invention the radial area of the pin 76 lies along the flat end face 96 thereof, different pin configurations still will provide at least a portion of known virtual radial area against which the pressure difference between the entrance 92 of the gap 90 and the exit 94 of the gap 90 will act on the pin 76 so that operation of the instrument 10 will be as described. The passage of the sample fluid 20 from the reservoir 18, through the gap 90, and back to the reservoir 18 as the shear viscosity is being measured reduces residence time of the sample fluid 20 in the gap 90. The reduced residence time, coupled with immersion of the gap 90 within the sample fluid 20 in the reservoir 18, reduces the effects of heating of the sample fluid 20 as the fluid passes through the gap 90 and aids in maintaining the sample fluid 20 at an essentially constant temperature for increased accuracy in the instrument 10. Thus, it will be seen that instrument 10 enables the accurate measurement of shear viscosity through the measurement of the force F by transducer 48, and does not rely upon measuring fluid pressure within the instrument with pressure-measurement transducers, thereby avoiding the attendant drawbacks of such pressure-measurement transducers. Further, the apparatus and method of the present invention enables the measurement of both the extensional viscosity and the shear viscosity of a sample fluid in basically the same instrument, with increased ease and economy.

It will be seen that the apparatus and method of the present invention attains the objects and advantages summarized above, namely, accomplishes the measurement of shear viscosity with increased sensitivity, thereby enabling accurate measurements, even in fluids of relatively low viscosity; enables an increased dynamic range for measuring a wider range of viscosities with increased accuracy; requires only a relatively short residence time of the sample fluid in the instrument for measurement of viscosity of the fluid, thereby reducing any tendency toward increasing the temperature of the fluid as the measurement is made; enables the measurement of both extensional viscosity and shear viscosity in the same basic apparatus, utilizing a relatively simple modification of a single instrument, thereby providing a greater amount of highly useful data at minimal additional expense; accomplishes ease of operation for accurate and reliable results with reduced complexity; and provides an instrument of relatively simple construction and reliable operation for service over a relatively long life.

It is to be understood that the above detailed description of a preferred embodiment of the invention is provided by way of example only. Various details of construction and procedure may be modified without departing from the true spirit and scope of the invention as set forth in the appended claims.

The embodiments of the invention in which an exclusive property or privilege is claimed are defined as follows:

1. Apparatus for measuring the shear viscosity of a fluid having given flow characteristics, a sample of which fluid is moved from a reservoir through a circuit in the apparatus, the apparatus comprising:
   a first member having a passage including an axially-extending inner surface;
   a second member having a portion of known radial area for location within the passage of the first member, the second member including an axially-extending outer surface for extending axially into the passage of the first member with at least a portion of the outer surface of the second member spaced radially from a corresponding portion of the inner surface of the first member to establish an axially-extending gap of predetermined radial and axial dimensions between the inner surface and the outer surface when the portion of known radial area is located within the passage, the gap including an entrance located within the passage of the first member, adjacent the portion of known radial area, and an axially opposite exit;
   metering means for moving the sample fluid through the circuit in the apparatus at a known volumetric flow rate, the metering means including means for establishing a pressure in the sample fluid at the entrance of the gap greater than the pressure in the sample fluid at the exit of the gap such that the sample fluid is urged through the gap as the fluid traverses the circuit, the predetermined radial and axial dimensions of the gap being related to the flow characteristics of the sample fluid such that the sample fluid is subjected to shear as the sample fluid passes through the gap; and
   force-measuring means for measuring the force urging one of the first and second members axially in the direction away from the other of the first and second members, as the sample fluid passes through the gap, which axially-directed force is indicative of the shear viscosity of the fluid.

2. The invention of claim 1 wherein the inner surface and the outer surface each are cylindrical and include a central axis.

3. The invention of claim 2 wherein the inner surface and the outer surface are located coaxially along the central axis of the surfaces and the gap has an annular cross-sectional configuration.

4. The invention of claim 3 wherein the central axis is oriented generally horizontally.

5. The invention of claim 1 wherein the force-measuring means is coupled with the second member for measuring force on the second member in the direction of flow of the sample fluid through the gap.

6. The invention claim 5 wherein the force-measuring means includes a force-rebalancing transducer such that no relative movement occurs between the first and second members during measurement of the axially-directed force.

7. The invention of claim 1 including temperature-control means for controlling temperature of the sample fluid so that the temperature of fluid passing through the gap is held essentially constant du measurement of the axially-directed force.

8. The invention of claim 1 including an arm having a near end and a far end, the near end being coupled to the force-measuring means and the far end carrying one of the first and second members, such that the far end of the arm and the one of the first and second members carried thereby may be immersed in the sample fluid in the reservoir during measurement of the axially-directed force.

9. The invention of claim 8 wherein the force-measuring means is a force-rebalancing transducer and the near end of the arm is affixed to the transducer such that the length of the arm between the near end and the far end serves as a lever arm in measuring the axially-directed force on the one of the first and second members carried at the far end of the arm.

10. The invention of claim 1 wherein:
   the first member comprises a sleeve, and the passage extends axially within the sleeve;
   the second member comprises a pin having a predetermined diameter establishing the portion of known radial area, and the outer surface extends axially along the pin; and
   the axially-directed force measured by the force-measuring means is the sum of the pressure of the sample fluid in the passage of the sleeve at the entrance of the gap acting upon the portion of known radial area, and the drag of the sample fluid acting upon the portion of the outer surface of the pin in the sleeve during measurement of the axially-directed force.

11. The invention of claim 10 wherein the inner surface and the outer surface each are cylindrical and include a central axis.

12. The invention of claim 11 wherein the inner surface and the outer surface are located coaxially along the central axis of the surfaces and the gap has an annular cross-sectional configuration.

13. The invention of claim 12 wherein the central axis is oriented generally horizontally.

14. The invention of claim 13 wherein the force-measuring means is coupled with the pin.

15. The invention of claim 14 wherein the force-measuring means includes a force-rebalancing transducer such that no relative movement occurs between the pin and the sleeve during measurement of the axially-directed force.

16. The invention of claim 15 including temperature-control means for controlling the temperature of the sample fluid so that the temperature of the fluid passing through the gap is held essentially constant during measurement of the axially-directed force.

17. The invention of claim 15 including an arm having a near end and a far end, the near end being coupled to the force-measuring means and the far end carrying the pin, such that the far end of the arm and the pin may be immersed in the sample fluid in the reservoir during measurement of the axially-directed force and the length of the arm between the near end and the far end serves as a lever arm in measuring the axially-directed force on the pin.

18. The method of measuring the shear viscosity of a sample fluid having given flow characteristics, the method comprising the steps of:

establishing an axially extending gap of predetermined radial and axial dimensions between a first member and a second member, the gap including an entrance and an exit;

moving the sample fluid through the gap and establishing a pressure in the sample fluid at the entrance of the gap greater than the pressure in the sample fluid at the exit of the gap so as to urge the sample fluid through the gap, from the entrance to the exit, at a known volumetric flow rate, the predetermined radial and axial dimensions of the gap being related to the flow characteristics of the simple fluid such that the sample fluid is subjected to shear as the sample fluid passes through the gap;

applying the pressure at the entrance of the gap to one of the first and second members to establish an axial force tending to move that one of the first and second members in the direction axially away from the other of the first and second members as the sample fluid passes through the gap; and measuring the total force tending to move the first and second members axially away from one another, as the sample fluid passes through the gap which total force is indicative of the shear viscosity of the sample fluid.

19. The invention of claim 18 wherein one of the first and second members extends axially into the other of the first and second members and includes a portion of known radial area located within the other of the first and second members, adjacent the entrance to the gap, and the pressure at the entrance to the gap is applied to the portion of known radial area.

20. Apparatus for measuring the shear viscosity of a sample fluid having given flow characteristics, the apparatus comprising:

a first member and a second member, and means for establishing an axially extending gap of predetermined radial and axial dimensions between the first member and the second member, the gap including an entrance and an exit;

means for moving the sample fluid through the gap and establishing a pressure in the sample fluid at the entrance of the gap greater than the pressure in the sample fluid at the exit of the gap so as to urge the sample fluid through the gap, from the entrance to the exit, at a known volumetric flow rate, the predetermined radial and axial dimensions of the gap being related to the flow characteristics of the sample fluid such that the sample fluid is subjected to shear as the sample fluid passes through the gap;

means for applying the pressure at the entrance of the gap to one of the first and second members to establish an axial force tending to move that one of the first and second members in the direction axially away from the other of the first and second members as the sample fluid passes through the gap; and means for measuring the total force tending to move the first and second members in the direction axially away from one another, as the sample fluid passes through the gap, which total force is indicative of the shear viscosity of the sample fluid.

21. The invention of claim 20 wherein one of the first and second members extends axially into the other of the first and second members and includes a portion of known radial area located within the other of the first and second members, adjacent the entrance of the gap, and the means for applying the pressure at the entrance of the gap applies that pressure to the portion of known radial area.

* * * * *